(12) United States Patent
Bloom et al.

(10) Patent No.: US 7,532,327 B2
(45) Date of Patent: May 12, 2009

(54) SYSTEMS AND METHODS FOR DETECTING SCATTERED LIGHT FROM A PARTICLE USING ILLUMINATION INCIDENT AT AN ANGLE

(75) Inventors: Scott H. Bloom, Encinitas, CA (US); John A. Adams, Escondido, CA (US); Kristina M. Crousore, Oceanside, CA (US); Alex Aguirre, San Diego, CA (US); Michael Tutrow, Solana Beach, CA (US); Brett A. Spivey, Carlsbad, CA (US)

(73) Assignee: JMAR Research, Inc., San Diego, CA (US)

( * ) Notice: Subject to any disclaimer, the term of this patent is extended or adjusted under 35 U.S.C. 154(b) by 113 days.

(21) Appl. No.: 11/231,350

(22) Filed: Sep. 19, 2005

(65) Prior Publication Data

US 2006/0227324 A1    Oct. 12, 2006

Related U.S. Application Data

(60) Provisional application No. 60/611,185, filed on Sep. 17, 2004.

(51) Int. Cl.
*G01N 21/00*    (2006.01)
(52) U.S. Cl. ...................................... 356/338; 356/337
(58) Field of Classification Search ........................ None
See application file for complete search history.

(56) References Cited

U.S. PATENT DOCUMENTS

| | | | |
|---|---|---|---|
| 3,871,769 A * | 3/1975 | Engel et al. .................. 356/336 |
| 4,167,335 A * | 9/1979 | Williams ..................... 356/336 |
| 4,548,473 A | 10/1985 | Lo et al. | |
| 4,548,500 A | 10/1985 | Wyatt et al. | |
| 4,710,025 A | 12/1987 | Wyatt et al. | |
| 4,716,123 A | 12/1987 | Wood | |
| 5,502,561 A * | 3/1996 | Hutchins et al. ............. 356/336 |
| 5,576,827 A * | 11/1996 | Strickland et al. ........... 356/336 |
| 5,721,433 A | 2/1998 | Kosaka | |
| 5,962,853 A | 10/1999 | Huth-Fehre et al. | |
| 6,016,712 A | 1/2000 | Warden et al. | |
| 6,091,492 A * | 7/2000 | Strickland et al. ........... 356/336 |
| 6,252,658 B1 * | 6/2001 | Togawa et al. .............. 356/335 |
| 6,347,374 B1 | 2/2002 | Drake et al. | |
| 6,407,812 B1 * | 6/2002 | Kurozumi et al. ........... 356/336 |
| 6,421,121 B1 | 7/2002 | Haavig et al. | |

(Continued)

OTHER PUBLICATIONS

PCT/US07/85975, International Search Report and Written Opinion of the International Searching Authority mailed Sep. 15, 2008.

(Continued)

*Primary Examiner*—Michael P Stafira
(74) *Attorney, Agent, or Firm*—Baker & McKenzie LLP

(57) ABSTRACT

A particle detection system uses illumination incident at an angle to detect particles in a liquid such as water. By using illumination incident at an angle, the scattered light can be measured through a range of angles that are greater than the measured range of angles produced when the illumination is incident at a normal angle, when using the same detector. For example, the light can be measured through an angle that is twice that produced with illumination incident at a normal angle.

34 Claims, 4 Drawing Sheets

U.S. PATENT DOCUMENTS

| | | | |
|---|---|---|---|
| 6,469,786 B2 * | 10/2002 | Shimaoka | 356/336 |
| 6,515,737 B2 | 2/2003 | Perry | |
| 6,519,033 B1 | 2/2003 | Quist et al. | |
| 6,541,627 B1 | 4/2003 | Ono et al. | |
| 6,573,992 B1 | 6/2003 | Drake | |
| 6,590,652 B2 | 7/2003 | Quist et al. | |
| 6,628,386 B2 | 9/2003 | Davis et al. | |
| 6,630,990 B2 | 10/2003 | van't Oever et al. | |
| 6,639,672 B2 | 10/2003 | Haavig et al. | |
| 6,760,107 B1 * | 7/2004 | Drake | 356/338 |
| 6,774,995 B2 | 8/2004 | Quist et al. | |
| 6,859,277 B2 | 2/2005 | Wagner et al. | |
| 6,934,022 B1 | 8/2005 | Engelhardt | |
| 6,972,424 B1 | 12/2005 | Quist et al. | |
| 7,057,724 B1 | 6/2006 | Mead et al. | |
| 7,072,038 B2 | 7/2006 | Quist et al. | |
| 2002/0186372 A1 | 12/2002 | Haavig et al. | |
| 2003/0035105 A1 | 2/2003 | Quist et al. | |
| 2003/0086087 A1 | 5/2003 | Quist et al. | |
| 2003/0090657 A1 | 5/2003 | Drake | |
| 2003/0107734 A1 | 6/2003 | Davis et al. | |
| 2004/0201845 A1 | 10/2004 | Quist et al. | |
| 2005/0151968 A1 | 7/2005 | Drake et al. | |
| 2006/0261941 A1 | 11/2006 | Drake et al. | |
| 2007/0013910 A1 | 1/2007 | Jiang et al. | |

OTHER PUBLICATIONS

PCT/US07/85976, International Search Report and Written Opinion of the International Searching Authority mailed Sep. 9, 2008.
PCT/US07/80609, International Search Report and Written Opinion of the International Searching Authority mailed Sep. 2, 2008.

* cited by examiner

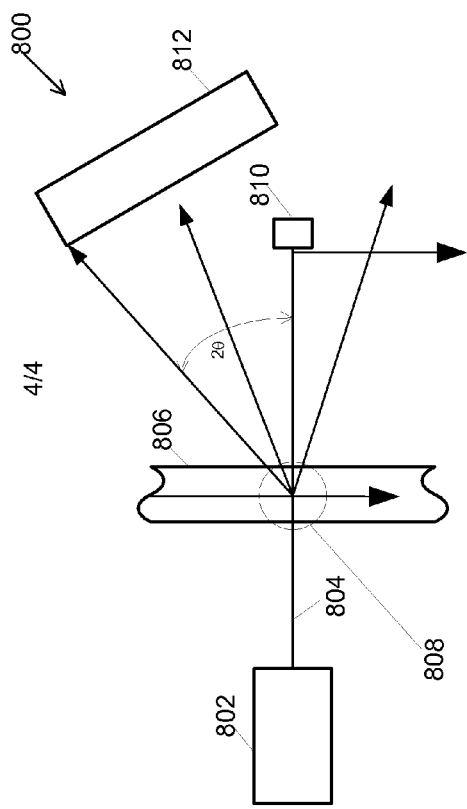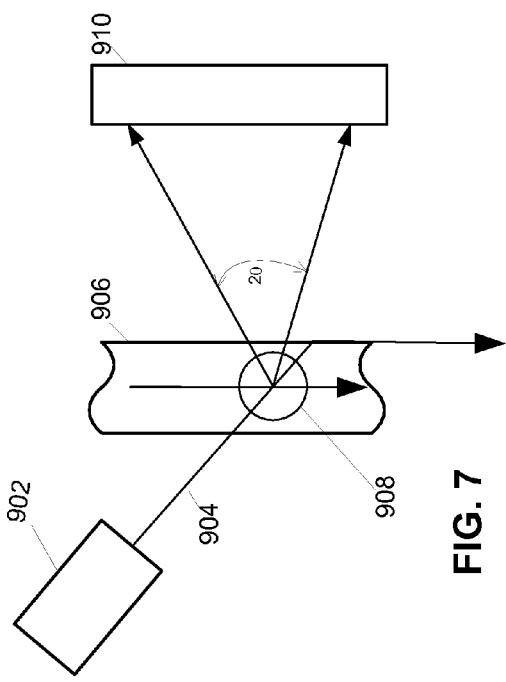
FIG. 6
FIG. 7

SYSTEMS AND METHODS FOR DETECTING SCATTERED LIGHT FROM A PARTICLE USING ILLUMINATION INCIDENT AT AN ANGLE

1. CROSS-REFERENCE TO RELATED APPLICATIONS

This application claims priority to U.S. Provisional Patent Application No. 60/611,185 filed on Sep. 17, 2004, entitled "Improvement in Resolution by Using Illumination Incident at an Angle," the entire contents of which is hereby incorporated by reference.

BACKGROUND

1. Field of the Invention

Embodiments of the invention relate to identifying particles, and in particular to identifying particles in a liquid using illumination incident at an angle.

2. Background of the Invention

A major concern for, e.g., water utilities is the detection and control of pathogenic microorganisms, both known and emerging, in potable water treatment and distribution. There are not only a number of chlorine resistant pathogens such as Cryptosporidium that can contaminate drinking water systems, but also potentially harmful microorganisms that can be introduced, either accidentally or intentionally, and propagate under suitable environmental conditions. Due to the length of time for standard laboratory methods to yield results, typically 24-72 hours, there has not been a reliable system to detect microbial contaminants in real-time and on line to provide a warning of pathogen contamination events. Because of these expanding challenges, there has been an accelerated development of rapid tests and real-time methods to address the pressing needs of the water treatment community.

Conventional microbiological methods can be used to detect some harmful microorganisms; however, such methods provide limit results. Analytical methods in microbiology were developed over 120 years ago and are very similar today. These methods incorporate the following steps: sampling, culturing and isolating the microbes in a suitable growth media by incubation, identifying the organisms through microscopic examination or stains, and quantifying the organisms. Cryptosporidium and Giardia form oocysts or cysts and cannot be cultured in conventional ways. To detect these protozoan pathogens, an amount of water containing suspected pathogens, typically 10 liters, is sent through a special filter to collect and concentrate the organisms. Then the filter is eluded and the organisms further processed, such as staining the organisms and sending the concentrated solution through flow cytometry for example. These procedures, which can be found in Standard Methods or ASME, require ascetic technique in sampling and handling, skilled technicians to perform the analysis, and a number of reagents, materials, and instruments to obtain results. Practically, such methods have, therefore, proved to be time consuming, costly, and of little effectiveness for many current environmental field applications.

In order to reduce the amount of time to access microbiological results, a number of methods have been developed, mostly in the field of medicine. These faster tests have been improved and adapted to the environmental field and are generally categorized as 1) accelerated/automated tests 2) rapid tests and 3) contamination warning systems (CWS).

Accelerated tests are by grab sample and results can be obtained in 4 hours to 18 hours. Accelerated tests include immunoassays, ATP luminescence, and fluorescent antibody fixation. Rapid tests are also by grab sample and require manipulation of the sample to 'tag' the microbes with an identifiable marker or concentrate the microbe's genetic material (DNA) for subsequent identification. Results are normally available in 1-3 hours. These types of tests include Polymerase Chain Reaction (PCR) and Flow Cytometry.

Real time contamination warning systems are continuous warning devices that detect contaminants and provide an 'event' warning within minutes to prompt further investigation or action. CWS include laser based multi-angle light scattering (MALS) and multi-parameter chemical & particle instruments that detect water quality changes inferring potential biological contamination. Continuous, real time detection of pathogens in water surveillance was first discovered in the late 1960's and has progressed through a series of development steps until the first public field demonstration in 2002.

MALS is an acronym for "multi-angle light scattering" and is based on laser technology, photo-detection, and computer signal processing. When coherent light strikes a particle, a characteristic scattering pattern is emitted. The scattering pattern encompasses many features of the particle including the size, shape, internal structures (morphology), particle surface, and material composition (organic or inorganic). Each type of microorganism will scatter light giving off a unique pattern called a 'bio-optical signature'. Photo-detectors collect the scattered light and capture the patterns which are then sent to an on-board computer. A microorganism's bio-optical signature is then compared against known pattern classifications in the detection library for results.

Presently, a detection system capable of meeting all of the 'ideal detection system' parameters, e.g., as cited by the American Water Works Association does not exist. Conventional MALS devices and methods often differ in the amount of time to obtain results, degree of specificity, sampling frequency, concentration sensitivity, operating complexity, and cost of ownership.

SUMMARY

A particle detection system uses illumination incident at an angle to detect particles in a liquid such as water. When the particles transit the laser beam, light is scattered in all directions and is described by MIE scattering theory for particles about the size of the wavelength of light and larger or Rayleigh Scattering when the particles are smaller than the wavelength of light. By using illumination incident at an angle, the scattered light can be detected over angles that are greater than obtainable when the illumination is incident at a normal angle using the same size detector. For example, the scattered light can be measured through an angle that is twice that produced with illumination incident at a normal angle.

In one aspect, the need for a beam stop included in the particle detecting system can be eliminated by using illumination incident at an angle.

These and other features, aspects, and embodiments of the invention are described below in the section entitled "Detailed Description."

In one aspect, a system for detecting and identifying a particle is described. The system can comprise an optical axis, a target zone, the optical axis intersecting the target zone, a detector configured to detect light scattered by a particle in the target zone, and a light source configured to generate a light beam and direct the light beam through the target zone at an angle, the angle formed relative to the optical axis.

In another aspect, a system for detecting and identifying a particle is described. The system can comprise an optical axis, a target zone, the optical axis intersecting the target zone, a detector configured to detect light scattered by a particle in the target zone, the detector positioned so as to capture scattered light rays scattered to an angle 2θ, and a light source configured to generate a light beam and direct the light beam through the target zone along the optical axis.

BRIEF DESCRIPTION OF THE DRAWINGS

Features, aspects, and embodiments of the inventions are described in conjunction with the attached drawings, in which:

FIG. 6 is a diagram illustrating an example particle detection system that implements the technique of FIGS. 3-5 in accordance with one embodiment; and FIG. 7 is a diagram illustrating an example particle detection system that implements the technique of FIGS. 3-5 in accordance with another embodiment.

DETAILED DESCRIPTION OF THE PREFERRED EMBODIMENTS

Figure 1:
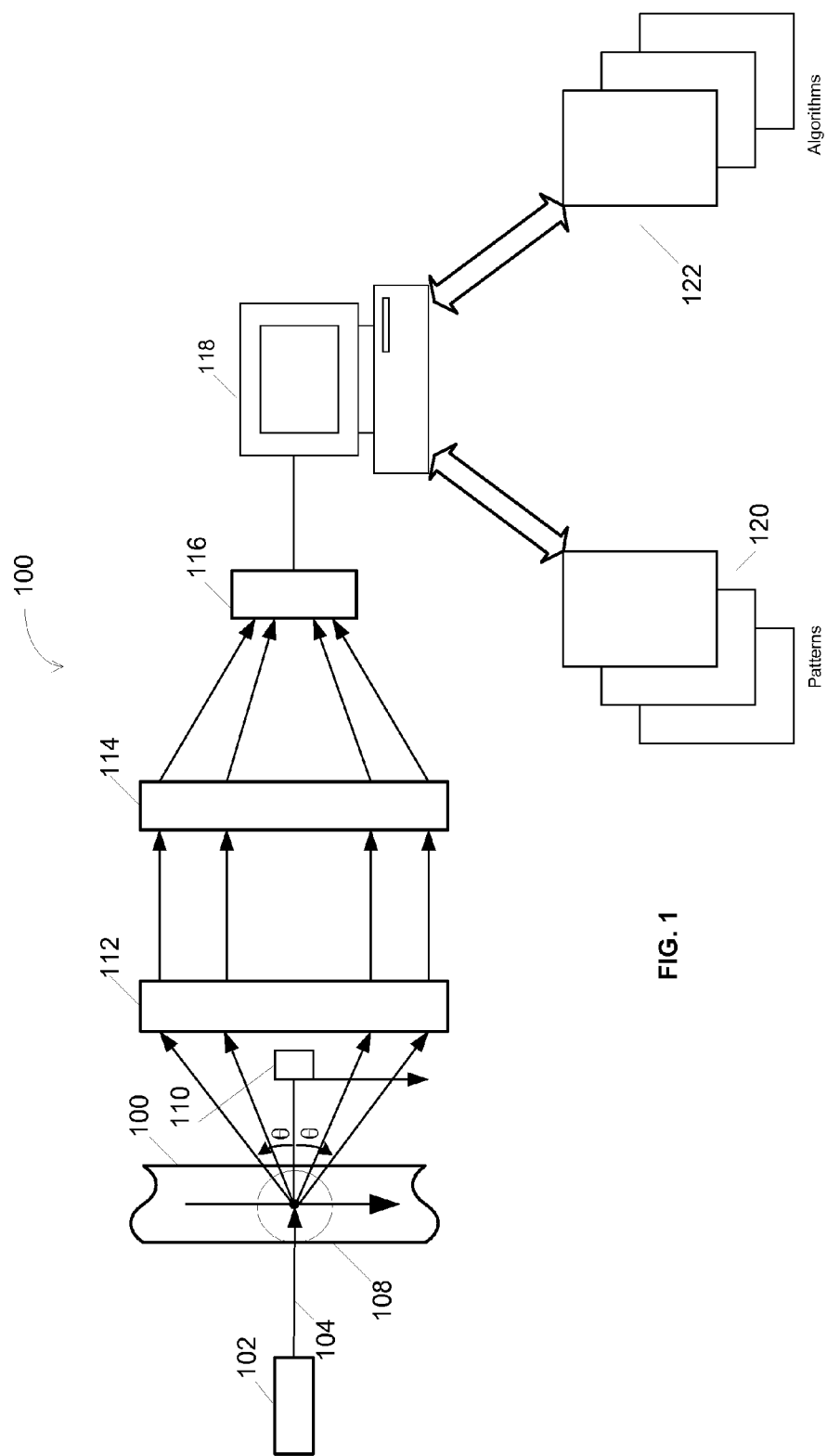
FIG. 1 is a diagram illustrating an example embodiment of a particle detection system.

In the following description, all numbers disclosed herein are approximate values, regardless whether the word "about" or "approximately" is used in connection therewith. They may vary by up to 1%, 2%, 5%, or sometimes 10 to 20%. Whenever a numerical range with a lower limit, $R_L$, and an upper limit $R_U$, is disclosed, any number R falling within the range is specifically and expressly disclosed. In particular, the following numbers R within the range are specifically disclosed: $R=R_L+k*(R_U-R_L)$, wherein k is a variable ranging from 1% to 100% with a 1% increment, i.e. k is 1%, 2%, 3%, 4%, 5%, ..., 50%, 51%, 52%, ..., 95%, 96%, 97%, 98%, 99%, or 100%. Moreover, any numerical range defined by two numbers, R, as defined in the above is also specifically disclosed. It is also emphasized that in accordance with standard practice, various features may not be drawn to scale. In fact, the dimensions of the various features may be arbitrarily increased or reduced for clarity of discussion.

Embodiments of the present invention provide a method for real-time particle detection that uses advancements in computing power, special optics, photonics engineering, advanced signal processing, and complex algorithms, in order to provide a MALS detection system that provides simplicity, cost effectiveness, speed, and reliability. The systems described in the embodiments below are analytical system using MALS where a side stream from a water source flows through a transparent flow cell. A laser directs a beam of light into the flow cell and through the water stream. In certain embodiments, the water is first characterized for background interferences to distinguish foreign particles from the pathogens' signatures resulting in a custom detection library in each particular installation.

In operation, particles pass through the beam, the scattered light is emitted and captured by the detectors, converted to a digital signal, and finally sent to the computer's microbial library for analysis. When a pattern is recognized by the library, the organisms are classified within minutes. The data can be transmitted to a user screen and remote communications equipment. In certain embodiments, upon reaching a pre-set threshold level, an 'alert' can be generated and an instantaneous sample can be automatically extracted for further identification and confirmation.

Water, or other liquids for that matter, can be monitored continuously as it passes through the flow cell at a defined rate. This provides a much higher probability of detecting and classifying microorganisms compared to intermittent grab samples. The speed and performance can be further enhanced when the 1) microbial concentration level is high, 2) the water, or liquid, is of high 'clarity' or purity, 3) microorganisms match defined bio-optical signatures in the library versus an 'unknown', and 4) the particles are of larger size, e.g., >1 micron, giving distinct scattering patterns.

In certain embodiments, if an unclassified organism is detected, the system can categorize it as an 'unknown' and still provide an 'alert' if a certain threshold level is reached.

Thus, the systems and methods described below can provide valuable early warnings of potential microbial contamination. The system described can be implemented economically and with extremely low operating costs. Further, the systems described do not use reagents or require costly consumables and can be compact, rugged, and easy to use, while requiring minimal operator training or expertise. In certain embodiments, 'warning' and 'alert' levels can be adjusted according to the requirements of a particular implementation and can interface with a number of communication protocols to provide immediate information for quality control or security personnel.

FIG. 1 is a diagram illustrating an example particle detection system configured in accordance with one embodiment of the systems and methods described herein. Many of the embodiments described below are used for detecting microorganism such as Cryptosporidium and Giardia; however, it will be understood that the systems and methods described herein can be used to detect any particle capable of detection using the systems and methods described, such as bacteria and yeasts. Bacteria are typically smaller than Cryptosporidium and Giardia ranging from 500 nanometers diameter upwards to 2 microns and from oval to rod shape. Yeasts are typically the size of Giardia or larger. Further, while the embodiments described below generally describe detected particles in water, it will be understood that the systems and methods described can be used to detect particles and other liquids, and even in other media such as air.

System 100 comprises a light source 102 configured to provide illumination 104 to a target area 108. In the embodiment of FIG. 1, target area 108 is within a fluid cell 106. Water intended to be interrogated for various particles, or microorganisms can flow through flow cell 106, e.g., in a downward direction as indicated. Illumination 104 will encounter particles in target zone 108, which will cause the illumination to scatter in a manner different than the illumination transmitted through the surrounding fluid medium.

System 100 can also comprise an optical system 124. Optical system 124 can comprise several elements. For example optical system 124 can comprise a lens, or lens system 112 as well as an optical element 114. The system 100 can also comprise a detector, detector system, or detector array 116, which can be interfaced with a processing system 118.

Light source 102 can be configured to deliver a structured light pattern, or illumination. Thus, light source 102 can be, e.g., a coherent light source, such as a laser. Depending on the embodiment, light source 102 can comprise a single light source, such as a single laser, or a plurality of light sources, such as a plurality of lasers. Further, the wavelength of the light source can be at a fixed wavelength. Alternatively, when multiple light sources are used, the light sources can have several discrete wavelengths.

Accordingly, light source 102 can be a laser configured to produce a laser beam 104. When laser beam 104 strikes a particle within target area 108, the particle will cause the beam to scatter in a pattern that is different than the pattern produced due to beam 104 traveling through the water flowing in flow cell 106. Optical system 124 can be configured to then pick up the scattered light and direct it onto detector 116.

Detector 116 can actually be a plurality of detectors, such as a plurality of detectors arrayed in different positions around target area 108. Alternatively, detector 116 can comprise an array of photo detectors. For example, in one embodiment, detector 116 can actually comprise a linear array of photo detectors configured to detect the scattered light and generate an electrical signal having an amplitude corresponding to the amplitude of the detected light. In one implementation for example, a Charge Coupled Device (CCD) can be used for detector 116. CCDs are readily available with thousands of pixels, wherein each pixel can form an individual photo detector.

Detector 116 can be configured to generate an electrical signal, or signals, reflective of the light pattern incident on detector 116. The signals can then be provided to processing system 118 for further analysis. As described above, processing system 118 can convert the signals into a pattern using various algorithms 122. Processing system 118 can also comprise the memory configured to store a plurality of optical signatures, or patterns 120 that are associated with various particles, or microorganisms of interest.

Thus, processing system can compare the pattern generated using algorithms 122 to one of the stored patterns 120 in order to identify particles within target zone 108.

As mentioned above, algorithms 122 and patterns 120 can be used to determine many features of particles being identified within target zone 108, e.g., including the size, shape, internal structures or morphology, particle surface, and material composition, i.e., organic or inorganic. For example, certain embodiments can use Multiple Analysis Of Variance (MANOVA) algorithms, neuro networks, simulated and annealing, algorithm independent machine learning, physiologic, grammatical methods, and other algorithmic techniques for pattern generation and recognition. It will be understood, however, that the systems and methods described herein are not limited to any specific algorithms or techniques, and that any algorithm or technique, or a combination thereof, that could be used to perform the processes described herein can be used as required by a particular implementation.

Particles within target zone 108 will cause light from laser beam 104 to scatter as illustrated in FIG. 1. Light scattering from target zone 108 at an angle greater than $\ominus$ from the optical axis of beam 104 will be internally reflected within flow cell 106 at the interface of flow cell 106 with the external atmosphere. Thus, only light at angles less than $\ominus$ can escape and be picked up by optical system 124.

In certain embodiments, a spherical lens (not shown) can be placed at the interface of flow cell 106 in order to allow light scattered at any angle to the lens to pass through the lens to optical system 124. Of course, including such a spherical lens increases the complexity and cost of system 100.

Light passing through target zone 108 along the optical axis of beam 104 will generally be of a much greater intensity than that of the scattered light beams. The intensity of the beam along the optical axis can be so great that it can essentially prevent, or degrade detection of the scattered light beams. Accordingly, a beam stop 110 can be included in order to deflect beam 104 and prevent it from entering optical system 124 and being detected by detector 116.

The light scattered by a particle within target zone 108 can enter optical system 124, which can comprise an optical element 114. Optical element 114 can be configured to direct the scattered light onto detector 116. Specifically, optical element 114 can be configured in such a way that it can direct light traveling along a given path to an appropriate position on detector 116 or to an appropriate detector within an array of detectors comprising detector 116. For example, in one embodiment, optical element 114 can be a holographic optical element constructed so that each refracting section refracts, or redirects light from one of the scattered paths so that it falls on the correct location of detector 116. In other embodiments, optical element 114 can comprise a zone plate lens that can be configured to map the distance from the central optical access to a unique mapping that is useful for high speed scanning.

In certain embodiments, the scattered light may need to be collimated after it passes through target zone 108. Thus, a converging lens 112 can be included in optical system 124. A converging lens can be configured to reduce the angle spread for the various scattered light rays. In other words, a converging lens can be configured to collimate or converge the spread light rays. In other embodiments, some other optical device can be used to collimate the scattered light rays. It will also be apparent, that certain embodiments may not need an optical lens 112, i.e., collimation may not be necessary depending on the embodiment. Thus, optical system 124 may or may not contain an optical lens 112, or a collimator, as required by the specific implementation.

As mentioned above, detector 116 can actually comprise a plurality of detectors such as a linear detector array or 2 dimensional array such as a Charge Coupled Device (CCD) or for better dynamic range, a 2 dimensional array of photodiodes or avalanche photodiodes. In one embodiment, for example, detector 116 can actually comprise a linear photo diode camera, e.g., a 128-pixel linear photo diode camera. In another embodiment, a square array of photodiodes may be used for detector 116. In yet another embodiment, an array of photodiodes arranged in segmented concentric circles may be employed for detector 116.

Generally, optical element 114 will be selected so as to complement detector 116 by directing the scattered light rays onto the appropriate pixel, or a section of detector 116; however, in certain embodiments, optical element 114 may not be needed. For example, in certain embodiments, the scattered light rays are incident directly onto detector 116.

Figure 2:
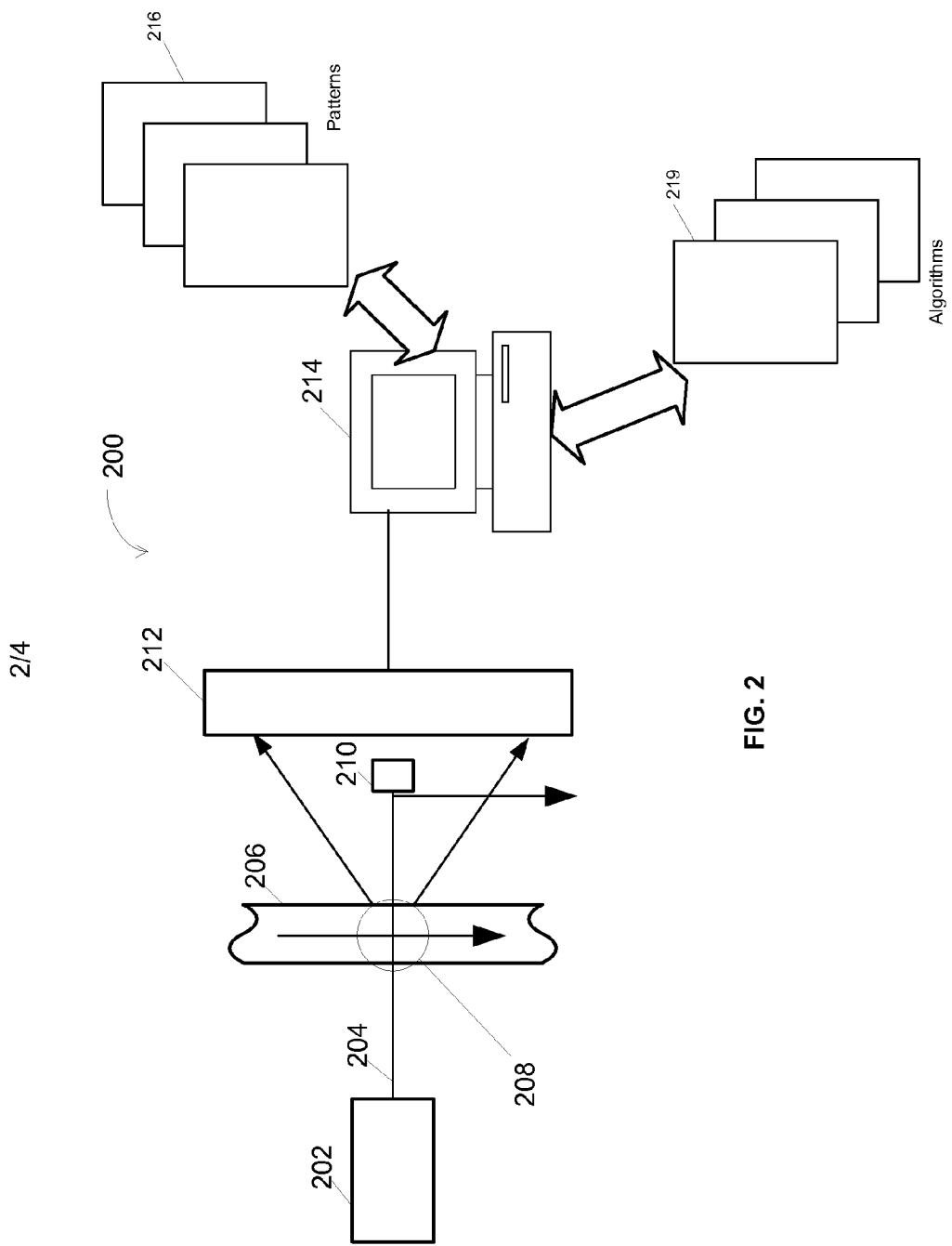
FIG. 2 is a diagram illustrating another example embodiment of a particle detection system.

FIG. 2 is a diagram of a particle detection system 200 that does not include an optical element. Thus, system 200 comprises a light source 202, such as a laser, that produces a beam 204 that is incident on particles in target zone 208 within a fluid flowing in flow cell 206. The particles scatter beam 204 and the scattered beams are then incident directly on a detector 212. Detector 212 then produces electrical signals based on the incident scattered light rays and provides the electrical signals to processing system 214. Processor system 214 can, like processing system 118, be configured to generate a pattern from the electrical signals using algorithms 218 and compare them against stored patterns 216 in order to identify particles within target zone 208.

In the embodiment of FIG. 2, a beam stop 210 is still required to reflect the light ray traveling along the optical axis.

For example, in one embodiment, detector 212 can comprise a 64-pixel detector array, while in other embodiments, detector 212 can comprise a 128-pixel detector array. It should also be noted, that detector 212 can comprise an Analog-to-Digital Converter (ADC) configured to convert analog signals produced by the detector arrays into digital signals that can be passed to processing system 214. For example, a system that uses a 64-pixel detector array can also include a 64-bit ADC, and a detector 212 that includes a 128-pixel detector array can include a 128-bit ADC.

Further, system 200 can include telescoping optics (not shown) in order to collimate the scattered light rays if necessary.

As mentioned above, each type of particle, or microorganism, will scatter light giving off a unique pattern called an optical signature, or bio-optical signature. A detector, such as detector 212, can collect the scattered light and capture the patterns. Electrical signals representative of the pattern can then be provided to a processing system such as processing system 214. This pattern can then be compared to stored patterns to aid in detection.

Figure 3:
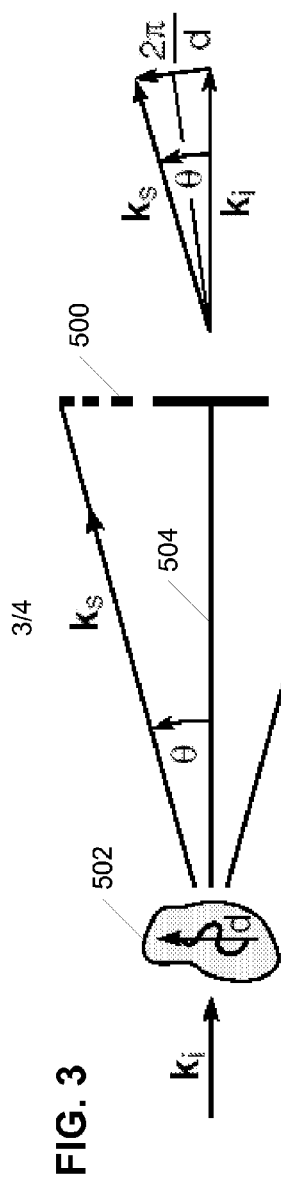
FIGS. 3-5 are diagrams illustrating a technique for using illumination incident at an angle in a light scattering detection system, such as the systems of FIGS. 1 and 2.

As noted above, if some form of spherical lens, or other device, is not used, then only scattered light rays with an angle less then ⊖ would be detected; however, if the illumination beam is incident at an angle, then light can be measured through twice the original measured scattering angles and still be captured by the detector. The scattering angle of the scattered radiation is inversely proportional to the size of the feature or object from which it was scattered, thus smaller features scatter light into larger angles. Illuminating the sample at angle permits radiation scattered from smaller features to still be captured by the detector's optical system thus, a greater resolution can be achieved. This is illustrated by FIGS. 3-5.

When illumination is incident upon a particle 502 along an optical axis 504, vector $k_i$ can be used to represent the illumination. As illumination incident along vector $k_i$ encounters particle 502, it will be scattered through a sphere of 360 degrees but only detected through a range of angles up to ⊖. Thus, a scattered light ray at the outer edge of the detector range can be represented by vector $k_s$.

Figure 4:
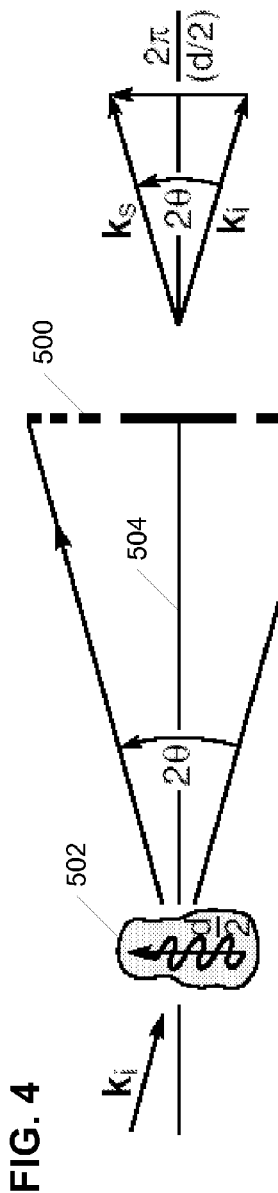

If, however, the illumination is incident at an angle illustrated by vector $k_i$ in FIG. 4, then the detector will be able to see light scattered through a greater range of angles. For example, the scattered light rays will be measured through an angle of 2⊖. As a result, objective 500 can collect scattered light rays scattered through twice the angle as compared to the system in FIG. 3. Thus, the resolution of the system illustrated in FIG. 4 would be twice that of the system illustrated in FIG. 3.

Figure 5:
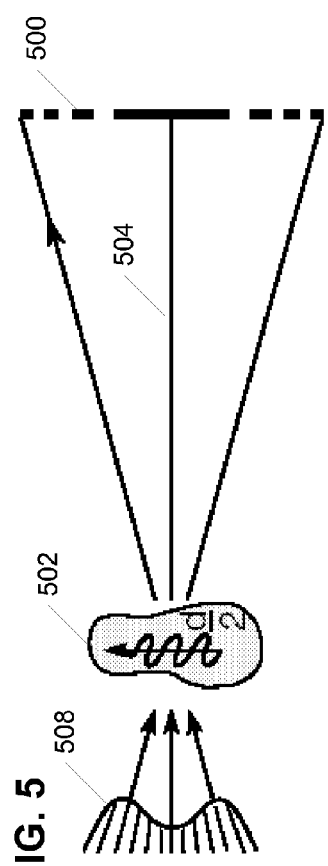

FIG. 5 is a diagram illustrating that the same effect can be achieved using a plurality of incident beams 508 that include beams incident at an angle from above and below the optical axis 504. Switching on or off the individual laser beams can provide additional multiple angles without having to provide additional detectors. If the switching is fast enough compared to the transit of the particle through the beam, then the additional angles can be obtained for the same particle.

It should be noted that objective 500 in FIGS. 3-5 can be a zone plate as well as another conventional optical element, including a holographic optical element.

FIGS. 6 and 7 illustrate that the technique depicted in FIGS. 4 and 5 could be achieved by altering the position of the optical detector or by configuring the light source so that the illumination is incident at an angle upon the target zone. Thus, FIG. 6 is a diagram illustrating an example particle detection system 800 in which an optical detector 812 has been repositioned so as to capture scattered light rays scattered to an angle 2⊖. In FIG. 6, a light source 802, such as a laser, produces a beam 804 that is incident on particles within target zone 808. It should be noted that a beam stop 810 can still be required within system 800 to deflect the beam traveling along the optical axis.

It will be understood that system 800 can comprise a processing system, but that such system is not illustrated for simplicity.

FIG. 7 is a diagram illustrating an example particle detection system 900 in which optical source 902 is configured such that beam 904 is incident upon target zone 908 at an angle equal to or greater than the critical angle defined by the phenomenon or total internal reflection. In the system of FIG. 7, by selecting the incident angle such that the beam experiences total internal reflection, the beam 904 is internally reflected within flow cell 906, and thus a beam stop is not required. This can lower the cost and complexity of system 900 and can, therefore, be preferable.

Again, it will be understood that system 900 can comprise a processing system, but that such system is not illustrated for simplicity.

While the invention has been described with respect to a limited number of embodiments, the specific features of one embodiment should not be attributed to other embodiments of the invention. No single embodiment is representative of all aspects of the inventions. Moreover, variations and modifications therefrom exist. For example, the magnetic memory devices and methods of storing data described herein can be used in any circuit using circuit design tools. In some embodiments, the devices are substantially free or essential free of any feature on specifically enumerated herein. Some embodiments of the method described herein consist of or consist essentially of the enumerated steps. The appended claims intend to cover all such variations and modifications as falling within the scope of the invention.

What is claimed:

1. A system for detecting and identifying a particle, the system comprising:
   an optical axis;
   a target zone, the optical axis intersecting the target zone;
   a detector configured to detect light scattered by a single particle in the target zone and generate signals based on the detected light scattered by the single particle;
   a light source configured to generate a light beam and direct the light beam through the target zone at an angle, the angle formed relative to the optical axis; and
   a processing system configured to receive signals from the detector, convert the signals into an optical pattern associated with the single particle, and compare the optical pattern associated with the single particle to at least one stored optical pattern.

2. The system of claim 1, further comprising an optical element configured to receive the scattered light and direct the received scattered light to the detector.

3. The system of claim 2, wherein the optical element is a holographic optical element.

4. The system of claim 2, wherein the optical element is a zone plate lens.

5. The system of claim 2, further comprising an optical lens configured to collimate the scattered light and direct the collimated scattered light to the optical element.

6. The system of claim 1, wherein the target zone is within a flow cell and wherein the particle in a fluid within the flow cell.

7. The system of claim 1, wherein the detector comprises a plurality of detectors.

8. The system of claim 7, wherein the plurality of detectors form a linear detector array.

9. The system of claim 7, wherein the plurality of detectors form a 2 dimensional array.

10. The system of claim 7, wherein the plurality of detectors form a Charge Coupled Device (CCD).

11. The system of claim 1, wherein the detector is a linear photo diode camera.

12. The system of claim 1, wherein the detector is a square array of photodiodes.

13. The system of claim 1, wherein the detector comprises an array of photodiodes arranged in segmented concentric circles.

14. The system of claim 1, further comprising a beam stop configured to deflect the light beam after it has passed through the target zone.

15. The system of claim 6, wherein the light beam is internally reflected by the interface of the flow cell with the atmosphere eliminating the need for a beam stop to deflect the light beam after it has traveled through the target zone.

16. The system of claim 2, further comprising a plurality of light sources each configured to produce a light beam, wherein at least some of the light beams are incident at an angel relative to the optical access.

17. The system of claim 16, wherein each of the plurality of light sources is switched on and off at a rate that is fast compared to the transit of the particle through the light beams.

18. A system for detecting and identifying a particle, the system comprising:
   an optical axis;
   a target zone, the optical axis intersecting the target zone;
   a detector configured to detect light scattered by a single particle in the target zone, the detector positioned so as to capture scattered light rays scattered to an angle $2\Theta$ and generate signals based on the detected light scattered by the single particle;
   a light source configured to generate a light beam and direct the light beam through the target zone along the optical axis; and
   a processing system configured to receive signals from the detector, convert the signals into an optical pattern associated with the single particle, and compare the optical pattern associated with the single particle to at least one stored optical pattern.

19. The system of claim 18, wherein the detector comprises a 64-pixel detector array.

20. The system of claim 18, wherein the detector comprises a 128-pixel detector array.

21. The system of claim 18, wherein the detector further comprises an Analog-to-Digital Converter (ADC) configured to convert analog signals produced by the detector into digital signals.

22. The system of claim 1, wherein the size of the particle detected is about 500 nanometers or greater.

23. The system of claim 1, wherein the size of the particle is between about 500 nanometers and about 2 micron.

24. The system of claim 1, wherein the size of the particle is above about 2 microns.

25. The system of claim 1, wherein the particle is non-spherical in shape.

26. The system of claim 1, wherein the particle is oval shaped.

27. The system of claim 1, wherein the particle is rod shaped.

28. The system of claim 1, wherein the light source is further configured to generate a plurality of light beams that include beams incident at an angle from above and below the optical axis, and direct the light beams through the target zone.

29. The system of claim 18, wherein the size of the particle detected is about 500 nanometers or greater.

30. The system of claim 18, wherein the size of the particle is between about 500 nanometers and about 2 micron.

31. The system of claim 18, wherein the size of the particle is above about 2 microns.

32. The system of claim 18, wherein the particle is non-spherical in shape.

33. The system of claim 18, wherein the particle is oval shaped.

34. The system of claim 18, wherein the particle is rod shaped.

* * * * *